United States Patent [19]

Davis et al.

[11] Patent Number: 5,565,075
[45] Date of Patent: Oct. 15, 1996

[54] ELECTROCHEMICAL GAS SENSOR FOR THE DETECTION OF NITRIC OXIDE

[75] Inventors: Brian K. Davis; Towner B. Scheffler, both of Butler, Pa.

[73] Assignee: Mine Safety Appliances Company, Pittsburgh, Pa.

[21] Appl. No.: 469,338

[22] Filed: Jun. 6, 1995

[51] Int. Cl.$^6$ .................................................. G01N 27/26
[52] U.S. Cl. .......................... 204/412; 204/291; 204/292; 204/431; 205/781
[58] Field of Search ............................. 204/153.18, 415, 204/412, 431, 291, 292; 205/781

[56] References Cited

U.S. PATENT DOCUMENTS

| | | | |
|---|---|---|---|
| 3,824,167 | 7/1974 | Oswin et al. | 204/415 |
| 4,169,779 | 10/1979 | Tataria et al. | 204/415 |
| 4,172,770 | 10/1979 | Semersky et al. | 204/412 |
| 4,474,648 | 10/1984 | Tantram et al. | 204/431 |
| 4,534,356 | 8/1985 | Papadakis | 204/415 |
| 4,536,274 | 8/1985 | Papadakis et al. | 204/415 |
| 4,790,925 | 12/1988 | Miller et al. | 204/415 |

*Primary Examiner*—T. Tung
*Attorney, Agent, or Firm*—Henry E. Bartony, Jr.; James G. Uber

[57] ABSTRACT

The present invention provides electrochemical sensors for the detection of nitric oxide comprising a housing in which is disposed a working electrode, a reference electrode and a counter electrode. The electrochemically active surface of the working electrode preferably comprises $RuO_2$. The nitric oxide electrochemical sensors of the present invention are capable of resolving nitric oxide concentrations at least as low as approximately 0.1 ppm and are well suited for use in medical environments because of their insensitivity to many other gases commonly used in medical environments.

7 Claims, 3 Drawing Sheets

ELECTROCHEMICAL GAS SENSOR FOR THE DETECTION OF NITRIC OXIDE

FIELD OF THE INVENTION

The present invention relates to an electrochemical gas sensor, and more particularly to an electrochemical gas sensor for the detection of nitric oxide (NO).

BACKGROUND OF THE INVENTION

Recently, nitric oxide (NO) has received a tremendous amount of attention in the medical community as a selective pulmonary vasodilator for use, for example, (i) in the treatment of pulmonary artery hypertension which is characteristic of severe adult respiratory distress syndrome and (ii) in certain types of surgery. See e.g., McArthur, C., "Putting NO to the Test," *The Journal for Respiratory Care Practitioners*, 29 (August/September 1994); Bigatello, L. M. et al., "Prolonged Inhalation of Low Concentrations of Nitric Oxide in Patients with Severe Adult Respiratory Distress Syndrome," *Anesthesiology*, 80:4, 761 (1994); and Feldman, P. L., "The Surprising Life of Nitric Oxide," *Chemical & Engineering News*, 26 (December 1993). Nitric oxide was first identified as an endogenous vasodilator in 1987. Inhaled nitric oxide has been shown to decrease pulmonary artery pressure in patients with pulmonary hypertension without systemic vasodilation. McArthur, supra.

However, nitric oxide can be toxic. Indeed, the Occupational Safety and Health Administration ("OSHA") has set the time-weighted average of inhaled NO at 25 ppm. Moreover, nitric oxide is an unstable molecule and combines readily with oxygen ($O_2$) to form nitrogen dioxide ($NO_2$), which has been shown to cause pulmonary toxicity at very low levels. McArthur, supra. Indeed, OSHA has set the upper limit of inhaled nitrogen dioxide at 5 ppm.

The nitrogen dioxide byproduct is thus potentially more toxic than the nitric oxide and can cause epithelial injury as well as airway hyperreactivity. The conversion of nitric oxide to nitrogen dioxide is dependent upon a number of factors including the nitric oxide dose, the inspired oxygen fraction ($FiO_2$), dwell time and temperature. Because of the toxicity of both nitric oxide and nitrogen dioxide, it is desirable to maintain the nitric oxide dose at the minimum level suitable to provide a desired therapeutic effect. In that regard, concentrations of nitric oxide as low as 2 ppm have been shown to be effective in improving arterial oxygenation and decreasing mean pulmonary artery pressure. Bigatello, et al., supra.

In light of their potential toxicity, it is recommended in treatment of patients with nitric oxide that nitric oxide and nitrogen dioxide concentrations be continuously monitored inline near the patient. McArthur, supra at 40. Moreover, the method/apparatus used to monitor such concentrations should be capable of resolving very low concentrations of such gases.

Chemiluminescent monitoring has been suggested for evaluating bedside/circuit levels of nitric oxide and nitrogen dioxide during delivery of therapeutic nitric oxide. McArthur, supra at 40–41. Although electrochemical gas sensors are less expensive, easy to use, and easily equipped with alarm systems, they are perceived to have a number of drawbacks in medical use. Most importantly, the sensitivity of electrochemical gas sensors has been questioned. Current electrochemical gas sensors are capable of resolving concentrations in parts per million, whereas chemiluminescent monitoring allows measurement of concentrations in parts per billion. Nevertheless, given the ease of use and inexpensive nature of electrochemical gas sensors it would be very desirable to develop such a sensor suitable for the monitoring of nitric oxide concentrations during therapeutic use.

In an electrochemical gas sensor, the gas to be measured (sometimes referred to as the analyte gas) typically diffuses from the test environment into the sensor housing through a gas porous or gas permeable membrane to a working electrode (sometimes called a sensing electrode) where a chemical reaction occurs. A complementary chemical reaction occurs at a second electrode known as a counter electrode (or an auxiliary electrode). The electrochemical sensor produces an analytical signal via the generation of a current arising directly from the oxidation or reduction of the analyte gas at the working electrode.

To be useful as an electrochemical sensor, a working and counter electrode combination must be capable of producing an electrical signal that is (1) related to the concentration of the analyte and (2) sufficiently strong to provide a signal-to-noise ratio suitable to distinguish between concentration levels of the analyte over the entire range of interest. In other words, the current flow between the working electrode and the counter electrode must be measurably proportional to the concentration of the analyte gas over the concentration range of interest.

In addition to a working electrode and a counter electrode, an electrochemical sensor often includes a third electrode, commonly referred to as a reference electrode. A reference electrode is used to maintain the working electrode at a known voltage or potential. The reference electrode should be physically and chemically stable in the electrolyte and carry the lowest possible current to maintain a constant potential.

Electrical connection between the working electrode and the counter electrode is maintained through an electrolyte. The primary functions of the electrolyte are: (1) to efficiently carry the ionic current; (2) to solubilize the analyte gas; (3) to support both the counter and the working electrode reactions; and (4) to form a stable reference potential with the reference electrode. The primary criteria for an electrolyte include the following: (1) electrochemical inertness; (2) ionic conductivity; (3) chemical inertness; (4) temperature stability; (5) low cost; (6) low toxicity; (7) low flammability; and (8) appropriate viscosity.

Electrochemical gas sensors of the type discussed above are generally disclosed and described in U.S. Pat. Nos. 4,132,616, 4,324,632, 4,474,648; and in European Patent Application No. 0 496 527 A1. A comprehensive discussion of electrochemical gas sensors is also provided in a paper by Cao, Z. and Stetter, J. R., entitled "Amperometric Gas Sensors," the disclosure of which is incorporated herein by reference.

In general, the electrodes of an electrochemical cell provide a surface at which an oxidation or a reduction reaction occurs (that is, an electrochemically active surface) to provide a mechanism whereby the ionic conduction of the electrolyte solution is coupled with the electron conduction of the electrode to provide a complete circuit for a current. It is generally believed that the half cell reactions of the working electrode and the counter electrode, respectively, for nitric oxide electrochemical gas sensors (using $H_2SO_4$ as the electrolyte) are as follows:

$$NO + 2H_2O \rightleftharpoons HNO_3 + 3H^+ + 3e^-$$

$$O_2 + 4H^+ + 4e^- \rightleftharpoons 2H_2O$$

The above reactions result in the following net cell reaction:

$$4NO + 2H_2O + 3O_2 \rightleftharpoons 4HNO_3$$

Although nitric oxide electrochemical gas sensors as described above have been used in industrial settings, current sensors are generally unsuitable for use in medical environments for a number of reasons. As discussed above, such sensors are generally incapable of accurately resolving concentration of nitric oxide foreseen to be used in medical therapy. Moreover, current nitric oxide electrochemical gas sensors such as the Nitric Oxide CiTicels® available from City Technology of Portsmouth, England are found to be sensitive to (or subject to interference from) other gases commonly used in the medical arts. Such interferent gases include, for example, nitrous oxide ($N_2O$), halothane, enflurane, and isoflurane, which are commonly used in anesthesia gases.

It is very desirable, therefore, to develop a nitric oxide electrochemical gas sensor suitable for use in the medical arts.

SUMMARY OF THE INVENTION

Accordingly, the present invention provides electrochemical gas sensors for the detection of nitric oxide suitable for use in the medical arts. In general, the electrochemical sensors of the present invention comprise a housing in which is disposed a working electrode, a reference electrode and a counter electrode. The electrochemically active surface of the working electrode preferably comprises ruthenium. More preferably, the electrochemically active surface of the working electrode preferably comprises ruthenium dioxide ($RuO_2$).

Suitable materials for the electrochemically active surface of the reference electrode include any nonpolarizable material generally known for use in reference electrodes. Preferably, however, such material is chosen to be (i) robust mechanically (that is, suitable to withstand relatively strong shock levels normally experienced during use of the sensor) and (ii) easy to prepare in a slurry or ink for coating upon a flexible membrane. Preferred materials for the electrochemically active surface of the reference electrode include electrically conductive carbons, platinum, iridium, combinations of electrically conductive carbon, platinum and iridium, and a mixture of silver (Ag) and silver sulfate ($AgSO_4$). The ratio of silver to silver sulfate is unimportant in such a mixture. The electrochemically active surface of the reference electrode preferably comprises platinum (Pt). Electrical connection is maintained between the working electrode and the counter electrode via an electrolyte present within the housing.

Suitable materials for the electrochemically active surface of the counter electrode include any material generally known for use in counter electrodes which is capable of making solution contact and providing a suitable surface for the reduction of oxygen. As with the reference electrode, such materials are preferably mechanically robust and easy to prepare in a slurry or ink. Preferred materials for the electrochemically active surface of the counter electrode include electrically conductive carbon, platinum, iridium and combinations of electrically conductive carbon, platinum and iridium. The electrochemically active surface of the counter electrode preferably comprises platinum.

As used in connection with the present invention, the phrase "electrically conductive carbon" refers generally to carbons preferably having resistances in the range of approximately 0.2 kΩ to 180 kΩ. Such resistances are measured with an ohmmeter, using a standard two-probe technique as known in the art wherein the probes are placed approximately 1.5 cm apart upon the surface of the electrode. Electrically conductive carbons for use in the present invention preferably also have surface areas in the range of 4.6 $m^2/g$ to 1500 $m^2/g$. A number of electrically conductive carbons suitable for use in the present invention are disclosed in U.S. patent application Ser. No. 08/426,271, the disclosure of which is incorporated herein by reference.

In fabricating the working electrode, reference electrode and counter electrode of the present invention, the electrochemically active material is preferably fixed upon a water resistant membrane such a GoreTex® film.

The nitric oxide electrochemical gas sensors of the present invention are capable of resolving nitric oxide concentrations at least as low as 0.1 ppm with a signal to noise (S/N) ratio of at least 2.0. Moreover, it has also been discovered that nitric oxide electrochemical gas sensors of the present invention are insensitive to the presence of many gases other than nitric oxide commonly present in medical environments. These gases include nitrous oxide, halothane, enflurane and isoflurane, which are commonly used as anesthetic gases. The present nitric oxide electrochemical gas sensors thus provide a significant improvement over current electrochemical sensors designed for the detection of nitric oxide which are generally unsuitable for use in medical environments.

DETAILED DESCRIPTION OF THE INVENTION

Figure 1:
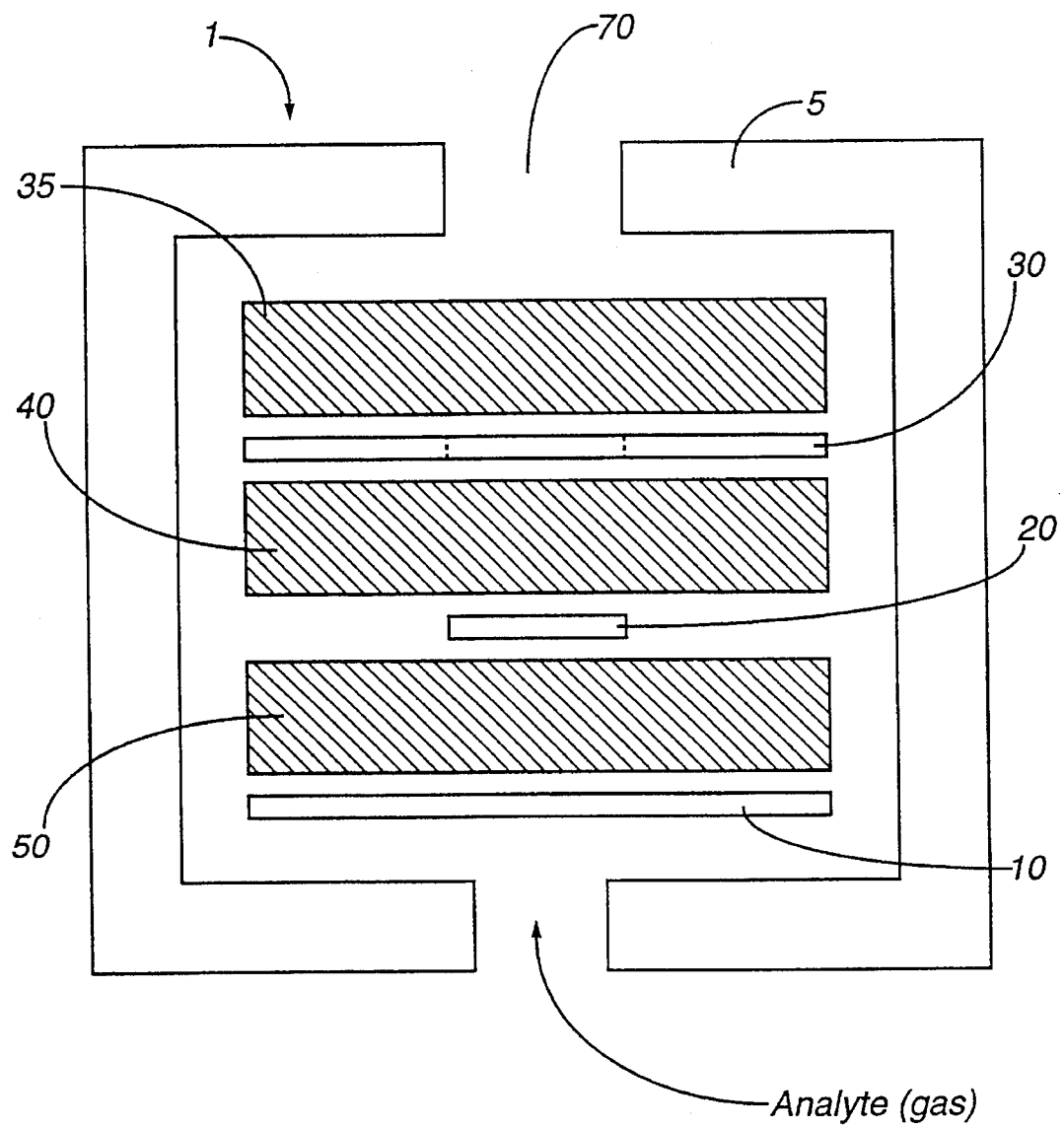
FIG. 1 illustrates schematically a cross-sectional view of an embodiment of an electrochemical gas sensor of the present invention.

As seen in FIG. 1, electrochemical nitric oxide sensor 1 preferably comprises a housing 5, enclosing a working electrode 10, a reference electrode 20 and a counter electrode 30. In fabricating electrochemical nitric oxide sensors 1 for use in the present studies, a porous spacer or wick 35 was first placed within housing 5. Counter electrode 30 was then placed into housing 5. A porous spacer or wick 40 was preferably then placed within housing 5 followed by reference electrode 20. A porous wick 50 was subsequently placed within housing 5 followed by working electrode 10.

After placement of working electrode 10 within housing 5, the perimeter of working electrode 10 was sealed, preferably via heat sealing, to housing 5. The interior of housing 5 was then filled with an electrolyte such as $H_2SO_4$ via opening 70. Upon filling of the interior of housing 5 with electrolyte, opening 70 was sealed, preferably via heat sealing using a water resistant membrane such as a GoreTex film (not shown). In the present studies, housing 5 was also placed within an outer housing (not shown). A detailed discussion of a preferred assembly for electrochemical gas sensor 1 is set forth in U.S. Pat. No. 5,338,429, the disclosure of which is incorporated herein by reference.

Wicks 40 and 50 operate to prevent physical contact of the electrodes but allow the liquid electrolyte to contact the electrodes and thereby provide ionic conduction and thus an electrical connection between working electrode 10 and counter electrode 30. Preferably, the electrolyte used in electrochemical nitric oxide sensor 1 is $H_2SO_4$.

The electrochemically active surface of working electrode 10 preferably comprises ruthenium (Ru) and, more preferably, ruthenium dioxide ($RuO_2$). Working electrodes 10 for use in electrochemical sensors 1 for the present studies were preferably fabricated via silk screen deposition of an ink comprising $RuO_2$. This ink was preferably deposited via silk screening upon a GoreTex film as known in the art. As also known in the art, GoreTex films provide a very good support for an electrochemically active material and also provide a good diffusion barrier, allowing analyte gas to diffuse into the electrochemical sensor while preventing escape of the liquid electrolyte. The $RuO_2$ ink may also be deposited using hand painting techniques as known in the art. Preferably, a film of $RuO_2$ having a thickness in the range of approximately 1 to 10 mil is deposited. The support for the $RuO_2$ film can comprise other electrically conductive materials such as, for example, electrically conductive carbon.

Suitable materials for the electrochemically active surface of reference electrode 20 include electrically conductive carbons, platinum, iridium, combinations of electrically conductive carbon, platinum and iridium, and a mixture of silver (Ag) and silver sulfate ($AgSO_4$). The electrochemically active surface of the reference electrode preferably comprises platinum (Pt).

In the case of platinum, reference electrodes 20 for use in electrochemical sensors 1 for the present studies were preferably fabricated via hand painting deposition of an ink comprising platinum powder. This ink was preferably deposited via hand painting upon a GoreTex film as known in the art. In the case of other materials as described above, the ink may also be deposited using silk screening techniques or hand painting techniques as known in the art. Preferably, a film of electrochemically active material having a thickness in the range of approximately 1 to 10 mil is deposited.

Suitable materials of the electrochemically active surface of counter electrode 30 include electrically conductive carbon, platinum, iridium and combinations of electrically conductive carbon, platinum and iridium. The electrochemically active surface of the counter electrode preferably comprises platinum. Such electrodes are preferably fabricated as discussed above for reference electrode 20.

After deposition of the films as described above, the films are preferably sintered to fix the electrochemically active material upon the substrate GoreTex such as is described in U.S. Pat. No. 4,790,925, the disclosure of which is incorporated herein by reference.

Figure 2:
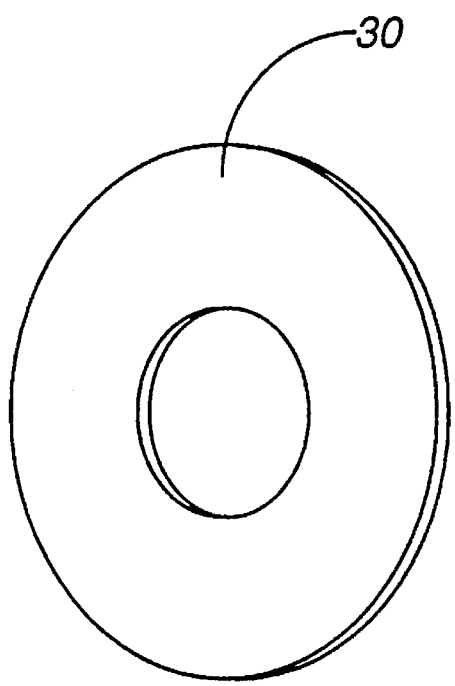
FIG. 2 illustrates a perspective view of an embodiment of the present counter electrode.
Figure 3:
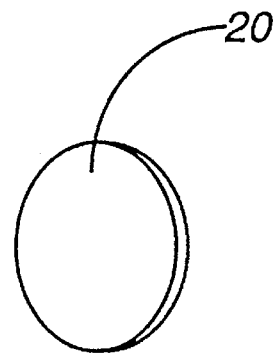
FIG. 3 illustrates a perspective view of an embodiment of the present reference electrode.

As illustrated in FIGS. 1 and 2, counter electrode 30 is preferably shaped in the general form of an annulus or ring. As illustrated in FIGS. 1 and 3, reference electrode 20 is preferably shaped in a generally circular form (that is, in the general shape of a disk). As clear to those skilled in the art, however, counter electrode 30, reference electrode 20 and working electrode 10 of electrochemical sensor 1 can be fabricated in many different shapes.

Preferably, electrochemical nitric oxide sensor 1 is subjected to a "cook-down" or "equilibration" period before use thereof to provide an adequately stable and low baseline. During the cook-down or equilibration period, electrochemical sensor 1 is stored at ambient conditions for a defined period of time. As common in the art, electrochemical sensor 1 is preferably maintained at a constant operating potential during the cook-down period. The operating potential of the electrochemical sensor 1 is preferably in the range of approximately +1000 mV to +1500 mV versus the normal hydrogen electrode ("NHE"). More preferably, the operating potential the electrochemical sensor 1 is in the range of approximately +1250 to +1350 mV versus the NHE.

Sensors 1 used in the present studies included a working electrode of RuO2 on GoreTex, a reference electrode of platinum of GoreTex and a counter electrode of platinum on GoreTex. These sensors were subjected to a potential of approximately +1300 mV (versus the NHE) during the cook-down period.

Preferably, a substantially stable baseline in the range of approximately 0 to 1 μA is achieved during the cook-down period for an electrode have a geometric surface area of approximately 1 cm$^2$. It has been found that a cook-down period of approximately 30 minutes is sufficient to provide an adequate baseline for electrochemical nitric oxide sensor 1. Briefer cook-down periods have not yet been investigated, however. Electrochemical nitric oxide sensors 1 used in the studies discussed below were subjected to a minimum cook-down period of 30 minutes. Preferably, a cook-down period of approximately 24 hours is allowed to ensure a stable baseline.

Studies of sensors 1 were performed under computer control in which ten (10) sensors could be tested simultaneously. A baseline reading for each sensor was established as the sensor output after a ten-minute exposure to air (0 ppm nitric oxide). In testing for nitric oxide concentration, air was first applied to electrochemical sensors 1 for ten (10) minutes followed by application of air having a known concentration of nitric oxide (for example, 100 ppm nitric oxide) for 10 minutes.

Response time and response time ratio (RTR) are empirical measures of the speed of response of a sensor and are critically dependent on the manner in which the test is performed (for example, the length of time the experiment lasts and/or the time at which the sensor reaches 100% of its final output). In the present studies, both response time and RTR were based upon a ten (10) minute exposure to test gas. RTR was calculated by dividing (i) the sensor output after one (1) minute of exposure to test gas by (ii) the sensor output after ten (10) minutes of exposure to nitrogen dioxide test gas. Based upon a ten-minute test, RTR is also the percentage of final response (that is, response or output obtained after ten minutes) obtained in one minute. Response time was generally recorded as the 90% response time ($t_{90}$). The $t_{90}$ response time is the time, in seconds, required for the sensor to reach 90% of the response or output obtained after ten minutes of exposure to test gas. The sensitivity (in units of μA/ppm nitric oxide) was established as the sensor output after ten (10) minutes of exposure to nitric oxide.

All the sensor cells studied had a pattern of five (5) inlet holes having an additive area approximately equal to the are of a single 19/64 in. hole to allow the test gas to enter the sensor cells. An average output of approximately 0.7 μA/ppm was obtained under these experimental conditions. As clear to one of ordinary skill in the art, sensitivity can generally be increased by increasing the total surface area of such inlet holes to allow more gas to enter the sensor cell.

The electrochemical sensors of the present invention were found to provide a substantially linear signal over at least the range of approximately 0 to 100 ppm nitric oxide. The response time of the present sensors was found to be less than approximately 35 seconds to 90% for sensors of any age and was found to be increase slightly with the age of the sensor.

The sensitivity of the present sensors, while maintained at a preferred operating bias of approximately + 1300 mV verses the NHE, was found to decrease slightly with increasing age to an age of approximately three (3) months at which time the sensitivity was found to stabilize. This "drift" in sensitivity is not expected to affect the performance of the present sensors, however, because the sensitivity remained well above that required to provide adequate resolution for medical use. Moreover, the drift occurred relatively slowly and would not be expected to cause significant error in output over time periods of expected in medical use (for example, time periods in the range of approximately three hours to 24 hours). Still further, frequent calibration of the sensor (as expected in medical use) should prevent significant errors.

The sensitivity of the present sensors was also found to be affected by humidity. In that regard, sensitivity was found to decrease if the sensor was stored in low humidity, whereas sensitivity was found to increase if the sensor was stored in a humid environment. In general, sensitivity was found to decrease if the sensors were stored in an environment having a relative humidity of less than approximately 15%. Preferably, therefore, the sensors of the present invention are stored in an environment having a relative humidity in the range of approximately 15 to 90%. It is believed that the drop in sensor sensitivity at low humidity is a result of loss of solution contact and/or changes in electrolyte conductivity. This "drying" and the resultant sensitivity loss at low humidity are reversible upon exposure of the sensor to ambient conditions in which the relative humidity is preferably in the range of approximately 15 to 90%.

The results of several interferent studies are set forth in Table 1. The data provided for each interferent gas correspond to the sensor output (that is, the indicated concentration of nitric oxide in ppm) upon exposure of the sensor to 100 ppm of the interferent gas. In Table 1, the results achieved with the present sensor are compared to the results achieved with Nitric Oxide CiTicel Model 7NT sensors available from City Technology. The data provided for the City Technology sensors were taken from the corresponding City Technology technical manual. The results indicate that the present sensor is generally less susceptible to erroneous results arising from the presence of the interferent gases studied than the City Technology sensor.

B, 5% halothane was introduced into the flowstream. At point C, the halothane was removed from the flowstream. At point D, 5% halothane was reintroduced into the flow stream. At point E, the halothane was once again removed from the flowstream. At point F, the nitrous oxide feed was removed from the flowstream and replaced with an equivalent amount of nitrogen. At point G, the nitric oxide feed was removed from the flowstream.

Figure 4:
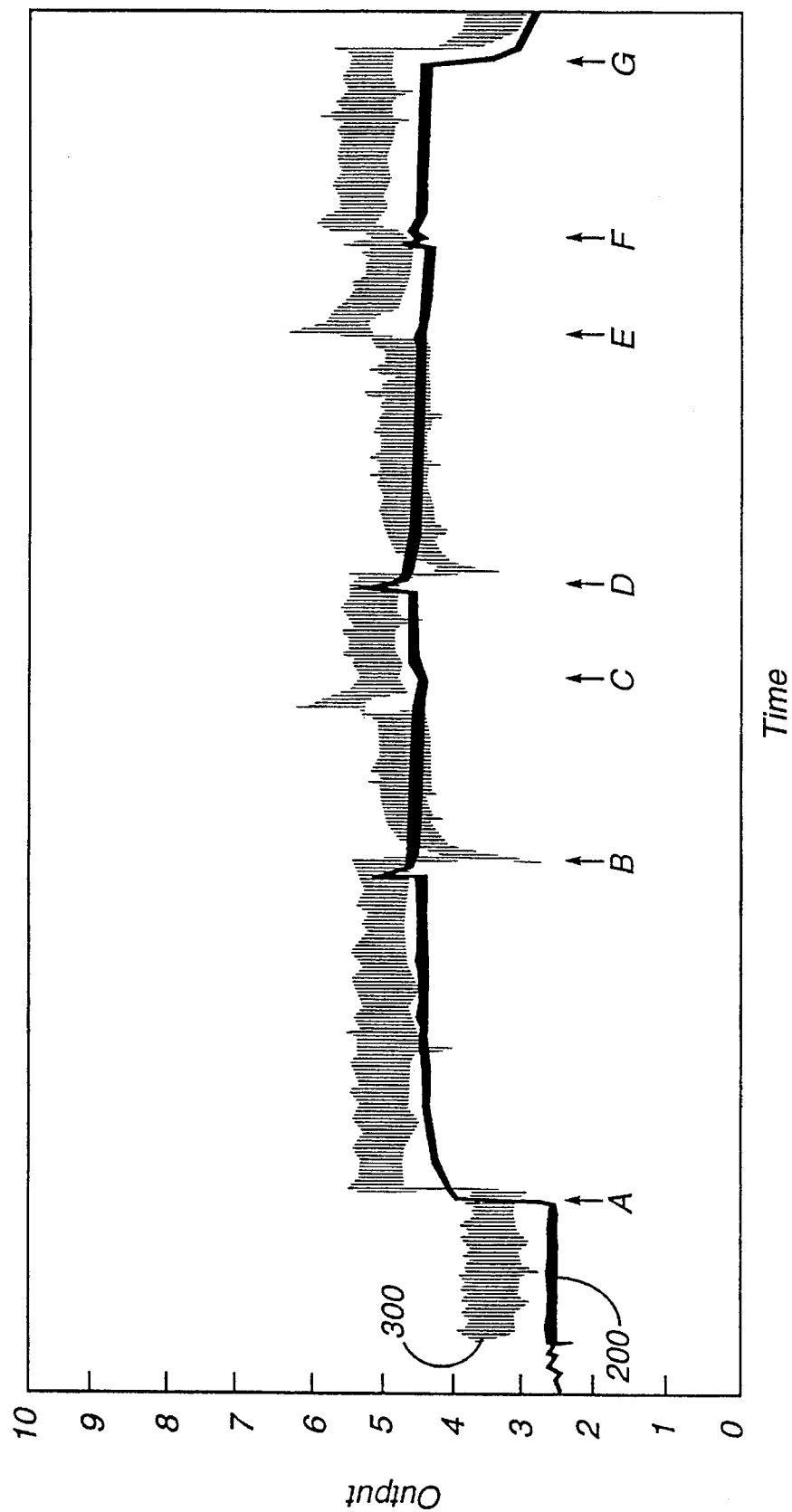
FIG. 4 illustrates an interferent study comparing the output of a sensor of the present invention with the output of a Nitric Oxide CiTicel sensor in the presence of several common anesthetic gases.

As illustrated in FIG. 4, the signal to noise ratio of the output of the present sensor is much greater than the signal to noise ratio of the output of the Nitric Oxide CiTicel sensor. For a signal to noise ratio of at least 2.0, the present sensor can resolve at least as low as about 0.1 ppm, whereas the Nitric Oxide CiTicel sensor can resolve only about 0.4 ppm.

Moreover, the output of the present sensor is much less susceptible to interference from halothane than the Nitric Oxide CiTicel sensor. Indeed, the upward oriented spike associated with the introduction of halothane at points B and D in line 200 (the output of the present sensor) is believed to the result of a sudden change in pressure resulting from the opening of a valve to release the halothane into the flowstream. Unlike the output of the Nitric Oxide CiTicel sensor (line 300), there is no corresponding downward spike upon removal of the halothane from the flowstream. No sudden pressure change accompanies the removal of the halothane from the flowstream. Similar results to those set forth in FIG. 4 were obtained with enflurane and isoflurane. The upward oriented spike at point F is believed to be a result of a sudden pressure change associated with the introduction of nitrogen into the flowstream.

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. An electrochemical gas sensor for the detection of nitric oxide, comprising: a housing, the housing having disposed therein a working electrode, a reference electrode and a counter electrode, an electrochemically active surface of the working electrode comprising a material selected from the group consisting of Ru and $RuO_2$, electrical connection being maintained between the working electrode and the counter electrode via an electrolyte present within the housing, the electrochemical gas sensor further comprising circuitry maintaining the working electrode at a potential in the range of approximately 1000 to 1500 mV versus a normal

TABLE 1

|  | NO | CO | $NO_2$ | $H_2S$ | $SO_2$ | HCN | HCl | $NH_3$ | $H_2$ | $C_2H_4$ | $Cl_2$ | $CO_2$ |
|---|---|---|---|---|---|---|---|---|---|---|---|---|
| Present Sensor | 100 | 0 | 3.4 | 59 | 0 | 0 | 16 | 0 | 0 | 0 | 0 | 0 |
| City Technology Sensor Model 7NT | 100 | 0 | <40 | ~35 | ~5 | 0 | <15 | — | 0 | 0 | 0 | — |

FIG. 4 illustrates a further interferent study in which halothane was introduced in into a flowstream containing 0.5 ppm nitric oxide to study the interferent effect thereof. Line 200 represent the output of the present sensor, while line 300 represents the output of a Nitric Oxide CiTicel Model 7NT sensor. At point A, 0.5 ppm nitric oxide was introduce into the flow stream, which initially comprised approximately 80% nitrous oxide and 20% oxygen. At point hydrogen electrode such that the working electrode is suitable for oxidizing nitric oxide.

2. The electrochemical gas sensor of claim 1, wherein an electrochemically active surface of the reference electrode comprises an electrochemically active material selected from the group consisting of an electrically conductive carbon, platinum, iridium and a mixture of silver and silver sulfate.

3. The electrochemical gas sensor of claim 1, wherein an electrochemically active surface of the counter electrode comprises an electrochemically active material selected from the group consisting of an electrically conductive carbon, platinum and iridium.

4. The electrochemical gas sensor of claim 1, wherein the electrochemically active surface of the working electrode comprises $RuO_2$.

5. The electrochemical gas sensor of claim 4, wherein the reference electrode comprises platinum.

6. The electrochemical gas sensor of claim 4, wherein the counter electrode comprises platinum.

7. The electrochemical gas sensor of claim 1, wherein the circuitry maintains the working electrode at a potential in the range of approximately 1250 to 1350 mV versus the normal hydrogen electrode.

\* \* \* \* \*